United States Patent [19]

Huang

[11] Patent Number: 4,612,660
[45] Date of Patent: Sep. 16, 1986

[54] TIME RESOLVED EXTENDED X-RAY ABSORPTION FINE STRUCTURE SPECTROMETER

[75] Inventor: Huey W. Huang, Houston, Tex.

[73] Assignee: The United States of America as represented by the Secretary of the Navy, Washington, D.C.

[21] Appl. No.: 734,986

[22] Filed: May 17, 1985

[51] Int. Cl.<sup>4</sup> .......................................... G01N 23/223
[52] U.S. Cl. ........................................ 378/44; 378/45
[58] Field of Search ..................... 378/44, 45, 46, 119, 378/120; 328/234, 235, 63, 72; 313/62

[56] References Cited

U.S. PATENT DOCUMENTS

| | | | |
|---|---|---|---|
| 2,848,624 | 8/1958 | Friedman et al. | 250/71 |
| 3,196,272 | 7/1965 | Culbertson | 250/833 |
| 3,404,275 | 10/1968 | Martinelli | 250/833 |
| 3,822,410 | 7/1974 | Madey | 378/119 |
| 4,134,012 | 1/1979 | Smallbone et al. | 250/272 |
| 4,317,994 | 3/1982 | Mallozzi et al. | 250/275 |
| 4,350,889 | 9/1982 | Lisnyansky | 378/46 |

OTHER PUBLICATIONS

Miyahara et al., "Sor-Ring: An Electron Storage Ring Dedicated to Spectroscopy", *Particle Accelerators*, vol. 7, No. 3, pp. 163-175, 1976.

*Primary Examiner*—Bruce C. Anderson
*Assistant Examiner*—Charles F. Wieland
*Attorney, Agent, or Firm*—Kenneth E. Walden; Frederick A. Wein

[57] ABSTRACT

The present invention relates to an X-ray spectrometer for obtaining EXAFS data from a target material. The target material is exposed to incident pulsed synchrotron/X-ray radiation having a selected range of continuous spectrum and intensity suitable for obtaining EXAFS data from the material. The transmitted or fluorescence X-rays is detected and integrated over a period of time. The integrator is controlled by a gate synchronous with the pulsed radiation. The integration time of the integrator can be varied. A xenon flash is provided for exciting appropriate materials and is controlled by a gating device which is also synchronized with the radiation pulses.

4 Claims, 6 Drawing Figures

TIME RESOLVED EXTENDED X-RAY ABSORPTION FINE STRUCTURE SPECTROMETER

BACKGROUND OF THE INVENTION

There are several processs which causes intensity loss of X-rays passing through matter. For X-ray quanta of wavelengths longer than a few tenths of 1 Å, say 0.5 Å, a primary process of X-ray absorption is the photoelectric effect. In this process the absorbed radiation energy is used for ejection of a low level electron from an atom. The photoelectron carries away any excess energy in the form of kinetic energy.

Since an electron can only be ejected from an inner shell if the quantum of the incident (X-ray) photon exceeds its bound energy, the X-ray absorption varies discontinuously with wavelength (or energy). The probability of ejection is largest for quanta of energy just exceeding the bound energy (called the absorption edge of the electron level, e.g., K-edge for the K-level electrons); it is small for a photon of energy very much in excess of that of the absorption edge.

When the atoms are in gas phase, the absorption coefficients decrease smoothly beyond an absorption edge as the energy X-ray quanta increases, until it reaches another absorption edge. But if the atoms are in liquid or solid phases, the absorption coefficients oscillate as the X-ray energy increases for a range of 1000 ev or so beyond an absorption edge. Such oscillation structures in the absorption coefficients are called extended X-ray absorption fine structure (EXAFS). The structures near absorption edges are called X-ray absorption near-edge structures (XANES). Both EXAFS and XANES are due to the influence of the neighboring atoms to the photoelectrons. As such both EXAFS and XANES contain information about the atomic arrangement near the absorbing atom. Therefore EXAFS and XANES are tools for studying local structures of matter.

The conventional methods for structure determination are the diffraction methods using X-ray, neutron beams or electron beams. However they are applicable only to structures with regular atomic arrangement, such as crystals. For materials lacking regularity, the diffraction method is much less useful. One can determine the local configuration of only relatively simple molecules. Although some insight to more complicated molecules can be gained from optical spectroscopy and magnetic resonance techniques, these techniques provide only indirect evidence from which the structural parameters of interest must be inferred. These limitations can be overcome by using EXAFS. The major requirement of performing EXAFS measurements is the availability of intense X-ray with a continuous spectrum. Thus, EXAFS has become a popular tool for structure determination only since synchrotron radiation has become available since the early 1970's. XANES is measured exactly the same way as EXAFS. It is difficult to obtain quantitative structural parameters from XANES, but it is very sensitive to the local chemistry, such as electronic distribution. So far XANES have been used only for qualitative analysis of local structures.

There are two standard ways of measuring EXAFS (and/or XANES). One is the transmission method in which one measures the incident and transmitted intensities of X-ray. The other is the fluorescence method in which one measures the incident and fluorescence intensities of X-rays. Recently with the advance of synchrotron radiation (SR) producing techniques, the intensity of SR has become so strong that one can measure EXAFS in a very short period of time. This opens the possibility of measuring time-resolved EXAFS of dynamic systems, from which one can infer the time-sequence of structural changes in a dynamic system. This is particularly useful for dynamic systems with relaxation times in the range of tens of microseconds to milliseconds, such as proteins in low temperature and solid structural changes near critical temperatures.

But the conventional methods of measuring either transmission or fluorescence EXAFS are inefficient for time-resolved measurements. Typically, the transmission EXAFS measurements involve a voltage to frequency converter with a maximum frequency of $10^6$ Hz; therefore it is difficult to measure an EXAFS point in less than 10 millisecond. The typical way of measuring fluorescence EXAFS is to use a counter to measure fluorescence intensity. The problem here is that synchrotron radiation is produced in pulses, typically one pulse per microsecond. Each pulse can contain $10^6$ photons per ev. In many cases a counter would intercept more than one fluorescence photons produced by such a pulse. The counter would count only one pulse no matter how many more fluorescence photons are intercepted. Therefore, in order to measure the changes in the EXAFS amplitude, one has to arrange the counter in such a way that no more than one fluorescence photon per SR pulse would be intercepted. This means that synchrotron radiation is not used to its full potential and the time-resolution cannot be improved even if the intensity of synchrotron radiation is further increased. Accordingly, the present invention is an EXAFS spectrometer which integrates the transmission X-ray or fluorescence X-ray over a chosen period of time (e.g. 100 microseconds, 1 millisecond, etc.) and makes the full use of intense synchrotron radiation, thus improving the time-resolution of time-resolved EXAFS measurements and automatically increasing measurement precision with the intensity of synchrotron radiation.

SUMMARY OF THE INVENTION

Briefly, the present invention relates to an X-ray spectrometer for obtaining EXAFS data from a target material. The target material is exposed to incident pulsed synchrotron/X-ray radiation having a selected range of continuous spectrum and intensity suitable for obtaining EXAFS data from the material. The transmitted or fluorescence X-rays is detected and integrated over a period of time. The integrator is controlled by a gate synchronous with the pulsed radiation. The integration time of the integrator can be varied. A xenon flash is provided for exciting appropriate materials and is controlled by a gating device which is also synchronized with the radiation pulses.

Accordingly, it is an object of the present invention to provide an EXAFS spectrometer having an integrator continuously variable and controllable by a gating means synchronous with the X-ray radiation pulses for improving the time resolution and the signal to noise ratio of time-resolved EXAFS measurements.

Another object of the present invention is to provide an EXAFS X-ray spectrometer having an integrator continuously variable and controllable by a gating means synchronous with the X-ray radiation pulses having a flash means controllable by another gating means and synchronous with the X-ray pulses for photolyzing an appropriate target material.

Further objects and advantages of the present invention will become apparent as the following description proceeds and features of novelty characterizing the invention will be pointed out with particularity in the claims annexed to and forming a part of this specification.

DESCRIPTION OF THE DRAWINGS

For a better understanding of the present invention reference may be had to the accompanying drawings wherein.

DETAILED DESCRIPTION OF THE PREFERRED EMBODIMENT

Figure 1:
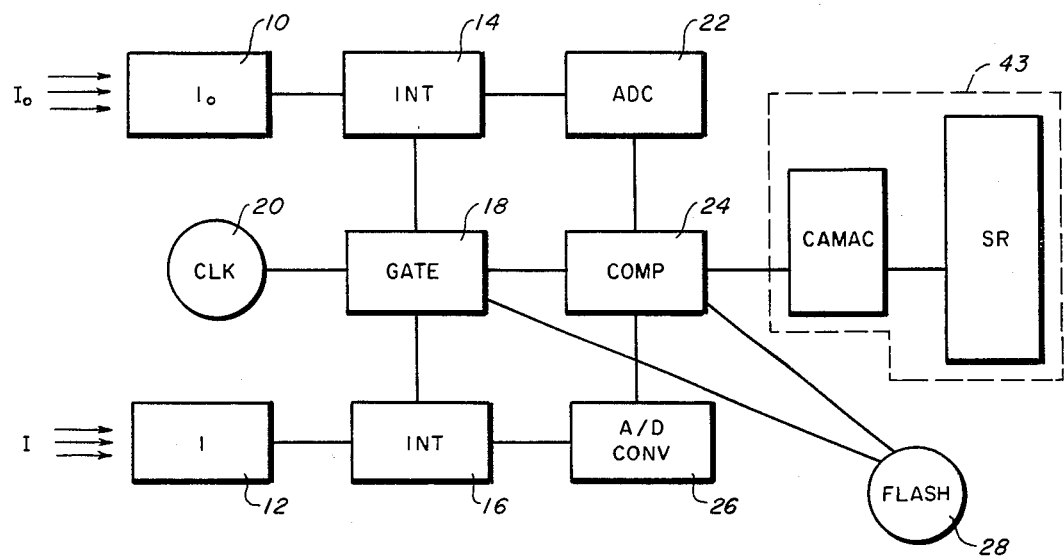
FIG. 1 is a schematic block diagram for the spectrometer of the present invention.

The X-ray absorption spectra of samples are measured form the K- or L-edge of a constituent element up to 1000 eV above the edge. The high energy part of the absorption spectra (EXAFS) can be used to determine the distances from the absorbing atom to its neighbors with accuracies of 0.01 Å, and the number of coordination around the absorbing atom can be determined to about ±20%. The near edge spectra are sensitive to many other factors, such as coordination symmetries and types of bondings, and consequently they are difficult to analyze quantitatively, but they are often useful in qualitative analyses. Since EXAFS is roughly a 1% modulation of the atomic absorption, an intense X-ray source with a continuous spectrum is needed for such measurements. For example, if the desirable signal to noise ratio is 10:1, one would need $10^6$ counts of signal per data point for a sample of a pure element. For samples of mixed elements (for example hemoglobin in which iron accounts for 10% of the total absorption at the iron K-edge), $10^8$ counts of signal per data point are often needed. Such photon intensities are easily obtained in synchrotron radiation laboratories. With the use of wigglers, beams of $10^{12}$ photons $eV^{-1} s^{-1}$ are routinely available. Hence one can measure each data point of, for example, the hemoglobin EXAFS with a sufficient signal to noise ratio in 100 μs. The present spectrometer is capable of measuring EXAFS with a time resolution continuously variable from 50 μs to 1000 μs. This enables the study of the transient structures of dynamic systems, for example, the changes of heme structure relative to the iron atom in hemoglobin at instances after photolysis and before the ligand recombination is completed. The limit for the time-resolution is entirely determined by the intensity of synchrotron radiation.

Because of its pulsed time structure and its high intensity, synchrotron radiation (SR) can not be directly measured with a photon counter. Electrons in synchrotrons or storage rings are grouped in bunches. In a typical synchrotron an electron bunch circles the storage ring at a frequency of 1.28 MHz ($\approx 1$ MHz for simplicity of this discussion). The width of the SR pulse from a bunch is 0.3 ns. Thus in the one-bunch mode, there is a 0.3 ns wide SR pulse repeating every 1 μs. The EXAFS beams typically give $10^{10}$–$10^{12}$ photons $ev^{-1}s^{-1}$. That means that each SR pulse consists of $10^4$–$10^6$ photons. Therefore, if one desires to measure a transient structure with a decay time less than 1 μs, one can synchronize the pulse clock with the sample stimulation and use only one SR pulse to measure EXAFS. However in order to achieve good statistics, repetition is necessary. If the decay time is milliseconds or longer one may desire to have a time resolution of, say 100 μs. In that case one can measure EXAFS with 100 consecutive pulses gated at a suitable time after the sample stimulation. This is accomplished in the present spectrometer with a charge integrator and a fast data acquisition system.

The basic idea is to measure an EXAFS point (at a given X-ray energy) over a short time interval $\tau$ at a time t measured from the time of sample excitation, and repeat the process at as many different energies as required. A series of points at different t can be measured for each sample excitation. In this disclosure, the intensity of the incident monochromatic X-ray is designated $I_o$ and the transmitted or fluorescent intensity is designated I. Both can be measured in either the counting mode or the integration mode. The statistics of the counting mode is intrinsically limited by the synchrotron radiation (SR) pulse frequency and the number of independent detectors used. The counting frequency of each detector must be set at a level lower than the SR pulse frequency at the highest SR intensity; otherwise the change in X-ray absorption would not be detected. Thus using the counting mode, one may not be able to take the full advantage of intense beams. Also when the beam intensity decreases during a measurement, the counting frequency, having been set for the highest intensity, may be unnecessarily sacrificed at low intensities, e.g., suppose that the optimal solid angle subtended by the fluorescence detector at the sample is $\Omega_1$ for an incident intensity $I_{01}$ and $\Omega_2$ for $I_{02}$ where $I_{01} > I_{02}$ and $\Omega_1 < \Omega_2$. For such a case, if $\Omega_2$ were used at $I_{01}$ the counting rate would saturate at the SR pulse frequency. But during a measurement one can only use a fixed setup, i.e. $\Omega_1$. Thus if the intensity decreases from $I_{01}$ to $I_{02}$, the counting rates at low intensities are lower than their optimal values. Thus, to make full use of intense SR beams, the integration mode should be used.

Referring now to the drawings where like members are designated with like numerals, there is shown in FIG. 1 a schematic diagram of the present spectrometer. The incident X-ray intensity, $I_o$, is measured with an ion chamber 10. The transmitted intensity, measured with another ion chamber 12, or the fluorescence intensity is measured with a scintillation detector 12. The spectrometer includes a pair of low-noise charge integrators 14, 16. Integrator 14 is used to integrate the output from the $I_o$ ion chamber 10. The integration interval $\tau$ is controlled with a gate circuit 18. The integration time t is synchronized with the synchrotron radiation (SR) pulse clock 20, so that each interval covers the same number of SR pulses. The output of the integrator 14 is read by an A/D converter 22 and recorded in a computer 24 which in this case is a microcomputer. The other integrator 16 is used to integrate the output I either from an ion chamber 12 or a fluorescence detector 12 as the case may be. The gating and recording systems for I are identical to that for $I_o$ and includes an A/D converter 26.

In the exemplary embodiment, a sample of carboxymyoglobin (MbCO) kept at 80° K. was used. The carbon monoxide bound to myoglobin can be photolyzed with a xenon flash 28. The present disclosed embodiment involves the photolysis with a flash 28 which is synchronous with the synchrotron radiation pulse. However, it is within the contemplation of the present invention that materials not requiring photolyzing can be investigated and in such a case the flash and flash required apparatus portions can be deleted.

Figure 2:
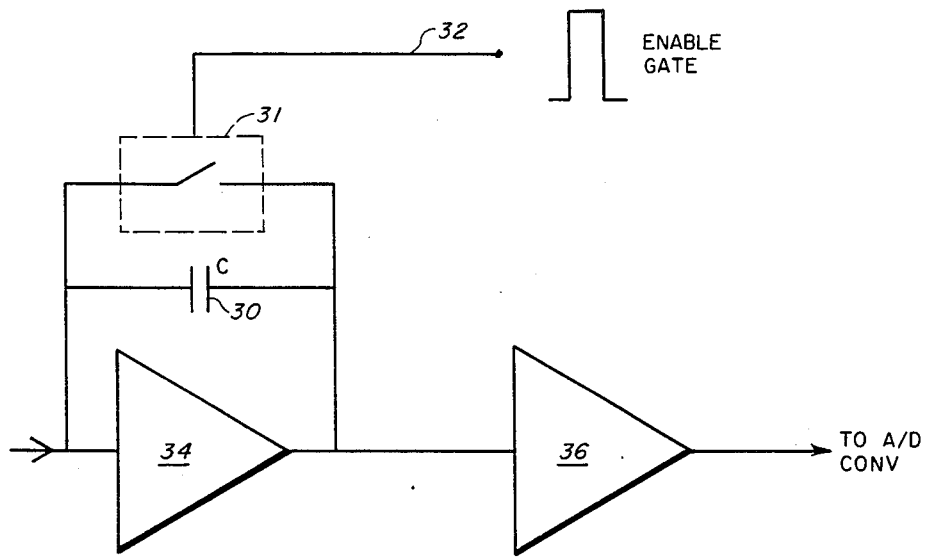
FIG. 2 is a schematic diagram of the integrator of the spectrometer of FIG. 1.

FIG. 2 shows the diagram for charge integrators 14, 16. It is basically an integration capacitor 30 and a MOSFET switch 31. An integration cycle is initiated when the enable gate 32 goes high and opens switch 31. The cycle ends when the enable gate 32 goes low and closes switch 31. The integration interval $\tau$ is then equal to the width of the gate pulse which is generated by an external gate circuit.

The integrator is built around a low-noise wideband chopper stabilized amplifier 34. To adjust the gain of signal there is included a variable gain amplifier 36 between the integrator 14 and the A/D converter 22. Special care should be taken to reduce the effects of leakage current and drift. The electronic noise of the integrator should be lower than the anode dark current ($10^{-10}$ amp) of the photomultiplier which is used in the I fluorescence detector 12.

Figure 3:
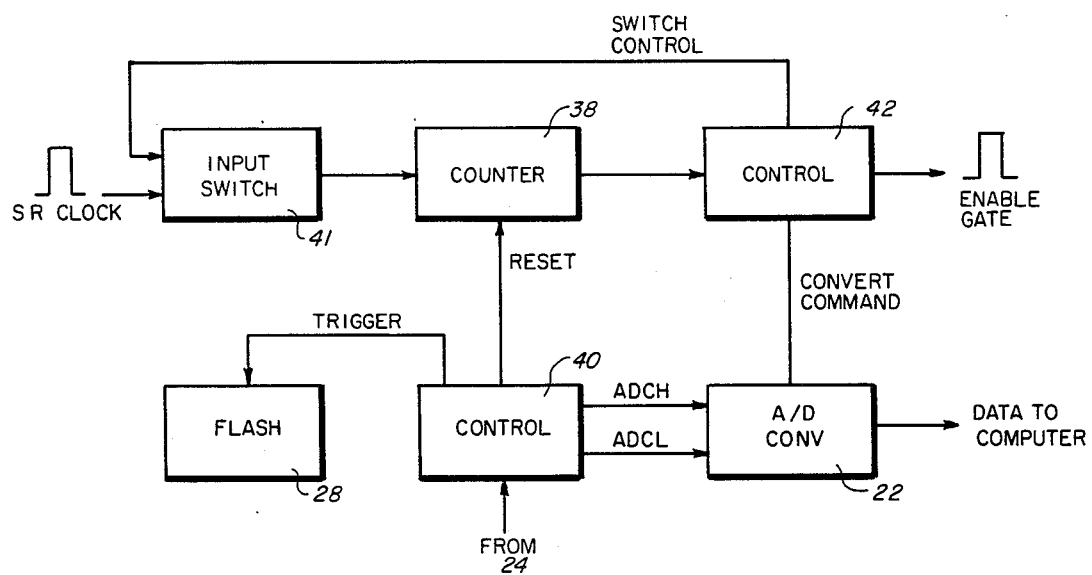
FIG. 3 is a schematic block diagram of the gating circuit of the spectrometer of FIG. 1.

The gate circuit 18 is shown in FIG. 3 and provides the counting, timing and a number of other control functions, and communicates with computer 24 via a parallel interface.

A counter 38 is used to count the pulses arriving from the SR clock, whose passage is controlled by input switch 41. At time t after a flash trigger signal is sent, the computer 24 sends a command to the control circuit 40 which resets the counter 38 and opens the input switch 41. When the counter 38 counts one, a control circuit 42 turns on the integration enable 32 (FIG. 2). When the counter 38 counts a preset number N, the control circuit 42 turns off the integration enable 32, shuts the input switch 41 and sends a convert command to the A/D converter 22.

The outputs ADCH and ADCL of the control circuit 40 respectively enable the high byte and the low byte of a datum to be transferred from the A/D converter's buffer to the computer 24. In the exemplary embodiment, the 14-bit conversion time is 25 $\mu$s. The process of recording data and resetting the gate circuit for each integration cycle requires another 75 $\mu$s. Thus there is needed 100 $\mu$s dead time between two consecutive integration cycles.

Figure 4:
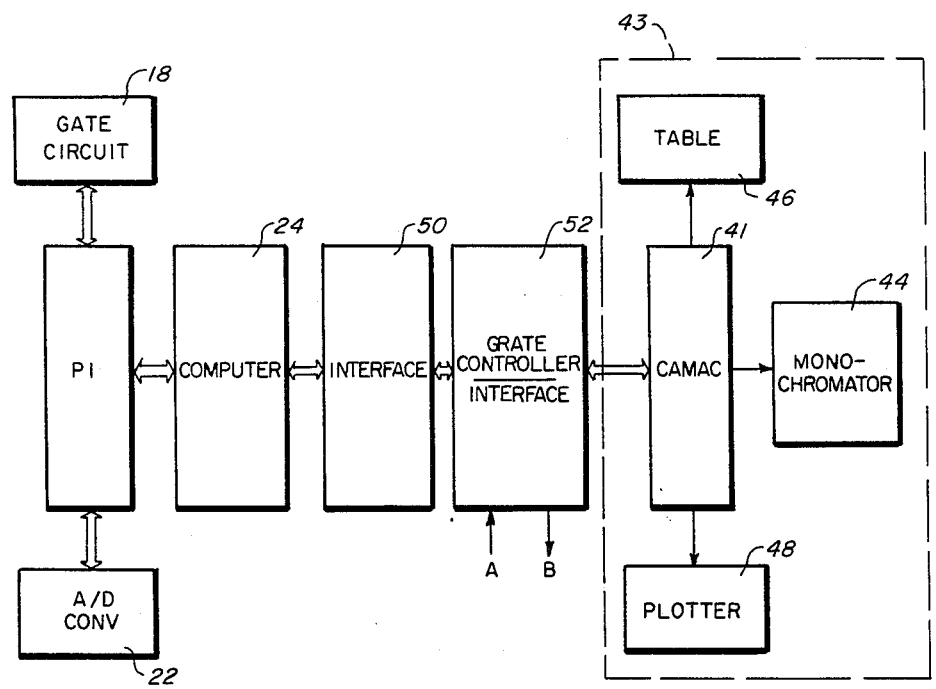
FIG. 4 is a schematic block diagram of the spectrometer of FIG. 1 with the addition of the synchrotron apparatus.

As shown in FIG. 4 the computer 24 interfaces with the gate circuit 18 and the A/D converter 22 on one hand and interfaces with the EXAFS instruments 43 in the synchrotron radiation laboratory on the other. Such laboratories typically use a CAMAC system 41 for controlling their EXAFS instruments 43 which include a monochromator 44, a sample table 46 in phase with the monochromator 44 and a graph plotter 48. The combination of an interface 50 and a CAMAC grate controller 52 allow the computer 24 to control and operate the EXAFS instruments. This feature permits the complete freedom in designing the EXAFS program, e.g., deletion of the flash 28 when not needed, as discussed hereinbefore.

Another interface 52 is a parallel interface having two 8-bit bidirectional I/O ports, commonly referred to as A side and B side. These ports are software programmable both in direction (input and output) and data value. The A port is used as an input port for receiving data from the A/D converters and the B port used as an output port for controlling the gate circuit.

Figure 5:
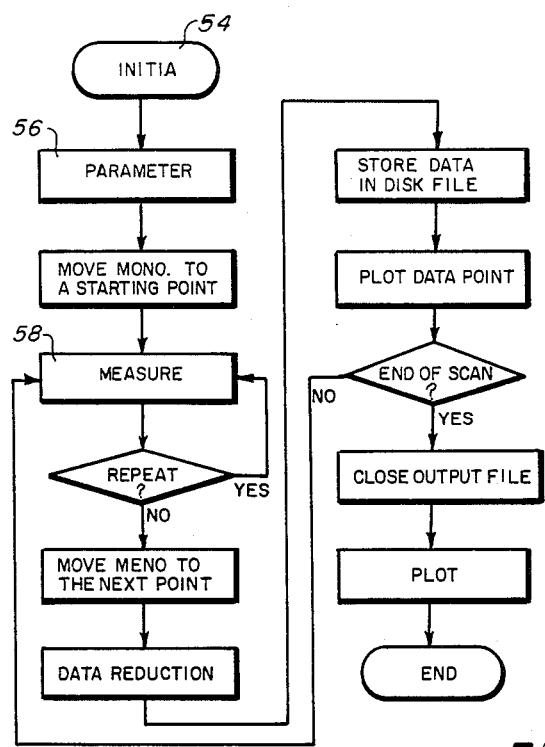
FIGS. 5 and 6 are flow chart diagrams of the time-resolved EXAFS program.
Figure 6:
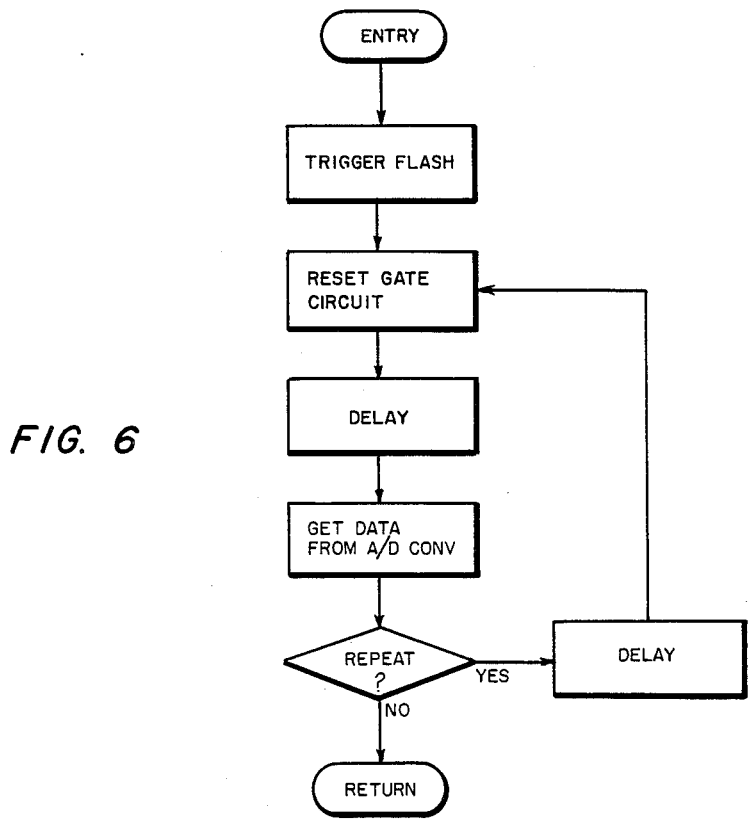

The flow chart of the time-resolved EXAFS program is shown in FIGS. 5 and 6. The function of INITIA 54 is to initiate the IEEE 488 interface, the CAMAC system and the parallel interface. The PARAMETER 56 program issues the experimental parameters, such as the monochromator angle, the scan range, point spacing, etc. to the various components of the system. The MEASURE 58 subroutine shown in FIG. 6 issues the reset command to the gate circuit to start its function as previously described. If the signal to noise ratio is not sufficient in one measurement, the same data point may need to be repeated. The required number of repetitions depends on the intensity of synchrotron radiation.

Thus, there is disclosed an X-ray spectrometer for obtaining EXAFS data from a target material exposed to pulsed synchrotron radiation having a selected spectrum and intensity suitable for obtaining EXAFS data from the material. The output from appropriate detectors such as scintillation detectors is fed to an integrator for improving the signal to noise ratio of the data. The time interval of integration is continuously variable over the range of 50 $\mu$s to 1000 $\mu$s with its starting time synchronous with the pulses of the synchrotron radiation. A flash also synchronized to the pulses of X-ray radiation by a gating means can be included for exciting the target material if appropriate.

While there has been illustrated and described what is at present considered to be the preferred embodiment of the present invention, it will be appreciated that numerous changes and modifications are likely to occur to those skilled in the art and it is intended in the appended claims to cover all those changes and modifications which fall within the true spirit and scope of the present invention.

What is claimed as new and desired to be secured by Letters Patent is:

1. An X-ray spectrometer for obtaining EXAFS data from a target material comprising:
    a means for detecting EXAFS data of a target material exposed to a pulsed synchrotron radiation having a selected spectrum and intensity suitable for obtaining EXAFS data from the material, and
    a means for processing said detection data, said means for processing comprising an integration means for measuring intensity of X-ray in such a way that maximizes the signal to noise ratio of the measurement, and a gating means for determining the time interval of integration and for synchronizing the starting time of integration with the pulses of synchrotron radiation.

2. The spectrometer of claim 1 wherein the integration time is continuously variable and controllable by the gating means over a predetermined range.

3. The spectrometer of claim 1 further comprising a flash means for exciting the target material.

4. The spectrometer of claim 3 wherein the flashing of the flash means is synchronized by a gating means to the pulses of the synchrotron radiation.

* * * * *